(12) United States Patent
Nikolic et al.

(10) Patent No.: US 7,887,477 B2
(45) Date of Patent: Feb. 15, 2011

(54) METHOD OF IMPROVING CARDIAC FUNCTION USING A POROUS MEMBRANE

(75) Inventors: Serjan D. Nikolic, San Francisco, CA (US); Hugh R. Sharkey, Redwood City, CA (US)

(73) Assignee: CardioKinetix, Inc., Menlo Park, CA (US)

( * ) Notice: Subject to any disclaimer, the term of this patent is extended or adjusted under 35 U.S.C. 154(b) by 526 days.

(21) Appl. No.: 10/302,272

(22) Filed: Nov. 22, 2002

(65) Prior Publication Data

US 2003/0105384 A1    Jun. 5, 2003

Related U.S. Application Data

(63) Continuation-in-part of application No. 10/212,033, filed on Aug. 1, 2002, now Pat. No. 7,303,526, which is a continuation-in-part of application No. 09/635,511, filed on Aug. 9, 2000, now abandoned.

(60) Provisional application No. 60/147,894, filed on Aug. 9, 1999.

(51) Int. Cl.
*A61N 1/362* (2006.01)

(52) U.S. Cl. ...................................... 600/16

(58) Field of Classification Search ................... 600/16, 600/37; 604/508; 606/213
See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,425,908 A | 1/1984 | Simon | |
| 4,619,246 A | 10/1986 | Molgaard-Nielsen et al. | |

(Continued)

FOREIGN PATENT DOCUMENTS

WO    WO 00/27292    5/2000

(Continued)

OTHER PUBLICATIONS

Kawata, et al., "Systolic and Diastolic Function After Patch Reconstruction of Left Ventricular Aneurysms," Ann.Thorac. Surg. 59, pp. 403-407, 1995.

(Continued)

*Primary Examiner*—Niketa I Patel
*Assistant Examiner*—Alyssa M Alter
(74) *Attorney, Agent, or Firm*—Shay Glenn LLP

(57) ABSTRACT

A porous membrane is inserted into a ventricle of a heart. The porous membrane creates a relatively hemostatic volume in which a thrombus can grow. Blood can still pass through fenestrations of the membrane into and out of the hemostatic volume. The fenestrations reduce pressures that act on the membrane, and so reduce stresses within the membrane. The flow characteristics through the hemostatic volume promote growth of the thrombus from a base of the hemostatic volume. The thrombus grows to slightly larger than the original size of the hemostatic volume so as to provide support for the membrane. Any remaining stresses within the membrane are thereby substantially eliminated. The thrombus shrinks over an ensuing period of time, with the membrane merely acting as a barrier to which an outer wall of the myocardium retracts. The function of the membrane is then complete, and may be absorbed.

32 Claims, 9 Drawing Sheets

U.S. PATENT DOCUMENTS

| | | | |
|---|---|---|---|
| 4,685,446 A | 8/1987 | Choy | |
| 4,710,192 A | 12/1987 | Liotta et al. | |
| 4,832,055 A | 5/1989 | Palestrant | |
| 4,917,089 A | 4/1990 | Sideris | |
| 5,104,399 A | 4/1992 | Lazarus | |
| 5,192,301 A | 3/1993 | Kamiya et al. | |
| 5,192,314 A * | 3/1993 | Daskalakis | 623/3.21 |
| 5,375,612 A | 12/1994 | Cottenceau et al. | |
| 5,385,156 A | 1/1995 | Oliva | |
| 5,425,744 A | 6/1995 | Fagan et al. | |
| 5,433,727 A | 7/1995 | Sideris | |
| 5,451,235 A | 9/1995 | Lock et al. | |
| 5,496,277 A | 3/1996 | Termin et al. | |
| 5,527,337 A | 6/1996 | Stack et al. | |
| 5,527,338 A | 6/1996 | Purdy | |
| 5,549,621 A | 8/1996 | Bessler et al. | |
| 5,578,069 A | 11/1996 | Miner, II | |
| 5,634,936 A * | 6/1997 | Linden et al. | 606/213 |
| 5,634,942 A | 6/1997 | Chevillon et al. | |
| 5,702,343 A | 12/1997 | Alferness | |
| 5,709,707 A | 1/1998 | Lock et al. | |
| 5,791,231 A | 8/1998 | Cohn et al. | |
| 5,797,849 A | 8/1998 | Vesely et al. | |
| 5,797,960 A | 8/1998 | Stevens et al. | |
| 5,829,447 A | 11/1998 | Stevens et al. | |
| 5,833,698 A | 11/1998 | Hinchliffe et al. | |
| 5,836,968 A | 11/1998 | Simon et al. | |
| 5,843,170 A | 12/1998 | Ahn | |
| 5,861,003 A | 1/1999 | Latson et al. | |
| 5,865,730 A | 2/1999 | Fox et al. | |
| 5,865,791 A | 2/1999 | Whayne et al. | |
| 5,871,017 A | 2/1999 | Mayer | |
| 5,875,782 A | 3/1999 | Ferrari et al. | |
| 5,876,325 A | 3/1999 | Mizuno et al. | |
| 5,876,449 A | 3/1999 | Starck et al. | |
| 5,879,366 A | 3/1999 | Shaw et al. | |
| 5,882,340 A | 3/1999 | Yoon | |
| 5,910,150 A | 6/1999 | Saadat | |
| 5,916,145 A | 6/1999 | Chu et al. | |
| 5,924,424 A | 7/1999 | Stevens et al. | |
| 5,925,062 A | 7/1999 | Purdy | |
| 5,925,076 A | 7/1999 | Inoue | |
| 5,928,260 A | 7/1999 | Chin et al. | |
| 5,961,440 A | 10/1999 | Schweich, Jr. et al. | |
| 5,961,539 A | 10/1999 | Northrup, III et al. | |
| 5,984,917 A | 11/1999 | Fleischman et al. | |
| 6,024,096 A | 2/2000 | Buckberg | |
| 6,024,756 A | 2/2000 | Huebsch et al. | |
| 6,045,497 A | 4/2000 | Schweich, et al. | |
| 6,059,715 A | 5/2000 | Schweich et al. | |
| 6,076,013 A | 6/2000 | Brennan et al. | |
| 6,077,214 A | 6/2000 | Mortier et al. | |
| 6,077,218 A | 6/2000 | Alferness | |
| 6,093,199 A | 7/2000 | Brown et al. | |
| 6,095,968 A | 8/2000 | Snyders | |
| 6,096,347 A | 8/2000 | Geddes et al. | |
| 6,099,832 A | 8/2000 | Mickle et al. | |
| 6,102,887 A | 8/2000 | Altman | |
| 6,125,852 A | 10/2000 | Stevens et al. | |
| 6,132,438 A | 10/2000 | Fleischman et al. | |
| 6,152,144 A * | 11/2000 | Lesh et al. | 128/898 |
| 6,161,543 A | 12/2000 | Cox et al. | |
| 6,193,731 B1 | 2/2001 | Oppelt et al. | |
| 6,221,092 B1 | 4/2001 | Koike et al. | |
| 6,231,561 B1 * | 5/2001 | Frazier et al. | 604/500 |
| 6,258,021 B1 | 7/2001 | Wilk | |
| 6,267,772 B1 | 7/2001 | Mulhauser et al. | |
| 6,290,674 B1 | 9/2001 | Roue et al. | |
| 6,312,446 B1 | 11/2001 | Huebsch et al. | |
| 6,328,727 B1 | 12/2001 | Frazier et al. | |
| 6,334,864 B1 | 1/2002 | Amplatz et al. | |
| 6,343,605 B1 | 2/2002 | Lafontaine | |
| 6,348,068 B1 | 2/2002 | Campbell et al. | |
| 6,355,052 B1 | 3/2002 | Neuss et al. | |
| 6,360,749 B1 | 3/2002 | Jayaraman | |
| 6,364,896 B1 | 4/2002 | Addis | |
| 6,387,042 B1 | 5/2002 | Herrero | |
| 6,406,420 B1 * | 6/2002 | McCarthy et al. | 600/16 |
| 6,419,669 B1 | 7/2002 | Frazier et al. | |
| 6,436,088 B2 | 8/2002 | Frazier et al. | |
| 6,450,171 B1 | 9/2002 | Buckberg et al. | |
| 6,482,228 B1 | 11/2002 | Norred | |
| 6,506,204 B2 | 1/2003 | Mazzocchi | |
| 6,511,496 B1 | 1/2003 | Huter et al. | |
| 6,537,198 B1 | 3/2003 | Vidlund et al. | |
| 6,551,303 B1 | 4/2003 | Van Tassel et al. | |
| 6,592,608 B2 | 7/2003 | Fisher et al. | |
| 6,652,555 B1 * | 11/2003 | VanTassel et al. | 606/200 |
| 6,685,627 B2 | 2/2004 | Jayaraman | |
| 6,730,108 B2 | 5/2004 | Van Tassel et al. | |
| 6,776,754 B1 | 8/2004 | Wilk | |
| 6,852,076 B2 | 2/2005 | Nikolic et al. | |
| 6,959,711 B2 | 11/2005 | Murphy et al. | |
| 6,994,093 B2 | 2/2006 | Murphy et al. | |
| 7,144,363 B2 | 12/2006 | Pai et al. | |
| 2001/0014800 A1 | 8/2001 | Frazier et al. | |
| 2002/0019580 A1 | 2/2002 | Lau et al. | |
| 2002/0026092 A1 * | 2/2002 | Buckberg et al. | 600/37 |
| 2002/0028981 A1 | 3/2002 | Lau et al. | |
| 2002/0032481 A1 | 3/2002 | Gabbay | |
| 2002/0055767 A1 | 5/2002 | Forde et al. | |
| 2002/0055775 A1 | 5/2002 | Carpentier et al. | |
| 2002/0111647 A1 | 8/2002 | Khairkhahan et al. | |
| 2002/0133227 A1 | 9/2002 | Murphy et al. | |
| 2002/0161394 A1 | 10/2002 | Macoviak et al. | |
| 2002/0169360 A1 | 11/2002 | Taylor et al. | |
| 2002/0188170 A1 | 12/2002 | Santamore et al. | |
| 2003/0045896 A1 | 3/2003 | Murphy et al. | |
| 2003/0050682 A1 | 3/2003 | Sharkey et al. | |
| 2003/0050685 A1 | 3/2003 | Nikolic et al. | |
| 2003/0105384 A1 | 6/2003 | Sharkey et al. | |
| 2003/0109770 A1 | 6/2003 | Sharkey et al. | |
| 2003/0120337 A1 | 6/2003 | Van Tassel et al. | |
| 2003/0181942 A1 | 9/2003 | Sutton et al. | |
| 2003/0220667 A1 | 11/2003 | Van Der Burg et al. | |
| 2004/0002626 A1 | 1/2004 | Feld et al. | |
| 2004/0034366 A1 | 2/2004 | van der Burg et al. | |
| 2004/0044361 A1 | 3/2004 | Frazier et al. | |
| 2004/0064014 A1 | 4/2004 | Melvin et al. | |
| 2004/0127935 A1 | 7/2004 | Van Tassel et al. | |
| 2004/0172042 A1 | 9/2004 | Suon et al. | |
| 2005/0007031 A1 | 1/2005 | Hyder | |
| 2005/0096498 A1 | 5/2005 | Houser et al. | |
| 2005/0154252 A1 | 7/2005 | Sharkey et al. | |
| 2005/0177180 A1 | 8/2005 | Kaganov et al. | |
| 2005/0197716 A1 | 9/2005 | Sharkey et al. | |
| 2005/0216052 A1 | 9/2005 | Mazzocchi et al. | |
| 2006/0014998 A1 | 1/2006 | Sharkey et al. | |
| 2006/0025800 A1 | 2/2006 | Suresh | |
| 2006/0030881 A1 | 2/2006 | Sharkey et al. | |
| 2009/0054723 A1 | 2/2009 | Khairkhahan et al. | |
| 2009/0062601 A1 | 3/2009 | Khairkhahan et al. | |
| 2009/0254195 A1 | 10/2009 | Khairkhahan et al. | |
| 2009/0287040 A1 | 11/2009 | Khairkhahan et al. | |

FOREIGN PATENT DOCUMENTS

| | | |
|---|---|---|
| WO | WO 01/30266 | 5/2001 |
| WO | WO 01/78825 A1 | 10/2001 |
| WO | WO 02/30335 | 4/2002 |
| WO | WO 02/071977 A2 | 9/2002 |
| WO | WO 2003/07778 A | 1/2003 |
| WO | WO 03/073961 A1 | 9/2003 |
| WO | WO 2004/012629 A | 2/2004 |

| WO | WO 2004/047679 A1 | 6/2004 |
| WO | WO 2004/100803 | 11/2004 |
| WO | WO 2005/007031 | 1/2005 |

OTHER PUBLICATIONS

Dor, "The Treatment of Refractory Ischemic Ventricular Tachycardia...," Seminars in Thoracic and Cardiovascular Surgery, vol. 9, No. 2, pp. 146-155, Apr. 1997.

Di Mattia, et al., "Surgical treatment of left ventricular post-infarction aneurysm...," European Journal of Cardio-thoracic Surgery 15, pp. 413-419, 1999.

Katsumata, et al., "An objective appraisal of partial left ventriculectomy...," Journal of Congestive Heart Failure and Circulator Support, pp. 97-106, 1999.

Dor, "Surgery for left ventricular aneurysm," Current Opinion in Cardiology, Current Science, pp. 773-780, 1990.

Dor, et al., "Ventricular remodeling in coronary artery disease," Current Opinion in Cardiology, Rapid Science Publishers, pp. 533-537, 1997.

AGA Medical Corporation, www.amplatzer.com/products, "The Muscular VSD Occluder" and "The Septal Occluder" device descriptions, Apr. 3, 2002.

Gore Medical, www.goremedical.com, "Helex Septal Occluder" product description, Apr. 3, 2002.

International Search Report and Written Opinion for PCT/US2004/014782 mailed Sep. 21, 2004.

Khairkhahan, et al., U.S. Appl. No. 10/436,959, entitled "System for improving cardiac function," filed May 12, 2003.

Khairkhahan, et al., U.S. Appl. No. 11/151,164, entitled "Peripheral seal for a ventricular partitioning device," filed Jun. 10, 2005.

Sharkey, et al., U.S. Appl. No. 11/199,633, entitled "Method for treating myocardial rupture," filed Aug. 9, 2005.

Khairkhahan, et al; U.S. Appl. No. 11/801,075, entitled "System for improving cardiac function," filed May 7, 2007.

Khairkhahan et al; U.S. Appl. No. 11/800,998, entitled "System for improving cardiac function," filed May 7, 2007.

Nikolic et al; U.S. Appl. No. 11/640,469, entitled "Cardiac device and methods of use thereof," filed Dec. 14, 2006.

Khairkhahan et al; U.S. Appl. No. 11/860,438 entitled "Laminar ventricular partitioning device," filed Sep. 24, 2007

Nikolic, et al., U.S. Appl. No. 12/129,443 entitled "Therapeutic methods and devices following mycardial infarction," filed May 29, 2008.

Khairkhahan et al; U.S. Appl. No. 12/125,015 entitled "Ventricular partitioning device," filed May 21, 2008.

Khairkhahan, Alexander; U.S. Appl. No. 12/181,282 entitled "Inflatable ventricular partitioning device," filed Jul. 28, 2008.

Khairkhahan et al; U.S. Appl. No. 12/198,022 entitled "Retrievable cardiac devices," filed Aug. 25, 2008.

Khairkhahan et al; U.S. Appl. No. 12/422,177 entitled "Sealing and filling ventricular partitioning devices to improve cardiac function," filed Apr. 10, 2009.

International Search Report and Written Opinion for PCT/US2005/000264 mailed Apr. 26, 2005.

* cited by examiner

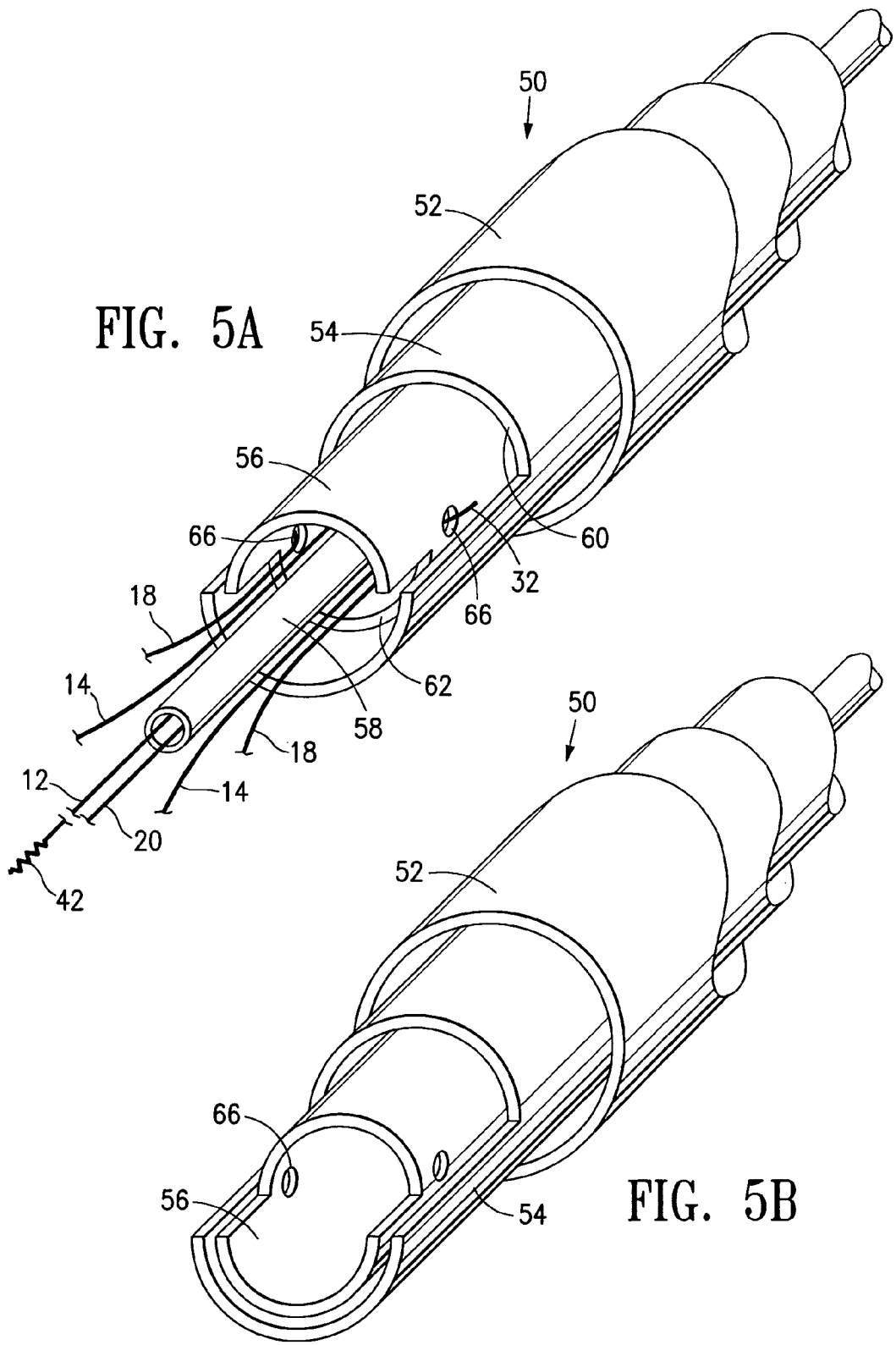

METHOD OF IMPROVING CARDIAC FUNCTION USING A POROUS MEMBRANE

CROSS-REFERENCE TO RELATED APPLICATIONS

The present patent application is a continuation-in-part of prior U.S. application Ser. No. 10/212,033, filed on Aug. 1, 2002, which is a continuation-in-part application of prior U.S. patent application Ser. No. 09/635,511, filed on Aug. 9, 2000, which claims priority from U.S. Provisional Patent Application No. 60/147,894 filed on Aug. 9, 1999, and are incorporated herein by reference in their entirety.

BACKGROUND OF THE INVENTION

1). Field of the Invention

This invention relates to a method and device for improving cardiac function.

2). Discussion of Related Art

Congestive heart failure annually leads to millions of hospital visits internationally. Congestive heart failure is a description given to a myriad of symptoms that can be the result of the heart's inability to meet the body's demand for blood flow. In certain pathological conditions, the ventricles of the heart become ineffective in pumping the blood, causing a back-up of pressure in the vascular system behind the ventricle.

The reduced effectiveness of the heart is usually due to damage to the heart muscle, leading to an enlargement of the heart. A myocardial ischaemia may, for example, cause a portion of a myocardium (of the heart muscle) to lose its ability to contract. Prolonged ischaemia can lead to infarction of a portion of the myocardium wherein the heart muscle dies and becomes scar tissue.

Once this tissue dies it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue, or even akinetic. As this situation worsens, the local area of compromised myocardium may in fact bulge out as the heart contracts, further decreasing the heart's ability to move blood forward. When local wall motion bulges out with each contraction, it is said to be dyskinetic. The dyskinetic portion of the myocardium may stretch and eventually form an aneurysmic bulge. Certain diseases may cause a global dilated myopathy (i.e., a general enlargement of the heart) when this situation continues for an extended period of time. As the heart begins to fail, the filling pressures increase, which stretches the ventricular chamber prior to contraction, greatly increasing pressure (preload) that the heart has to contract against. In response, the heart tissue remodels to accommodate the chronically increased filling pressures, further increasing the work that the now-compromised myocardium must perform.

This vicious cycle of cardiac failure results in the symptoms of congestive heart failure such as shortness of breath, edema in the periphery, nocturnal dypsnia (a characteristic shortness of breath that occurs at night after going to bed), weight gain, and fatigue, to name a few. The enlargement increases stress on the myocardium. The stress increase requires a larger amount of oxygen supply, which can result in exhaustion of the myocardium leading to a reduced cardiac output of the heart.

SUMMARY OF THE INVENTION

This invention relates to a device for improving cardiac function. The device includes a membrane which is insertable into a ventricle of a heart in a partitioning position, wherein the membrane substantially forms a division between two volumes of the ventricle, namely a first hemodynamic volume and a second relatively hemostatic volume of the ventricle. Blood enters the first hemodynamic volume through an inflow heart valve, circulates through and is contained primarily in the first hemodynamic volume, and leaves the first hemodynamic volume through an outflow heart valve. The membrane partitioning the first and second volumes confines the passage of blood through the heart to the first hemodynamic volume.

The membrane has a plurality of fenestrations that are sufficiently large to allow blood from the hemodynamic volume to flow therethrough into the hemostatic volume, for purposes of forming a thrombus in the hemostatic volume. The fenestrations are sufficiently small so as to allow formation of the thrombus within the hemostatic volume by isolating a volume of blood on the static side of the partition and sufficiently reducing flow so as to promote coagulation of that volume of blood. The device thereby predictably and purposefully produces a thrombus contained within the second volume of the chamber.

The device further includes at least one anchor formation connected to the membrane, the anchor formation having at least one anchoring portion that is positioned and capable of anchoring to tissue of a myocardium of the heart, and so anchor the membrane in the partitioning position to the myocardium.

The invention also relates to a method for improving cardiac function. A membrane having a plurality of fenestrations is inserted into a ventricle of the heart. The membrane is anchored to a myocardium of the heart in a partitioning position, wherein the membrane substantially forms a division between a first hemodynamic volume of the heart and a second relatively hemostatic volume of the heart. Blood enters the hemodynamic volume through a first respective heart valve, and leaves the hemodynamic volume through a second respective heart valve. The fenestrations are sufficiently large so that blood flows from the hemodynamic volume therethrough into the hemostatic volume, but sufficiently small so that a thrombus grows within the hemostatic volume.

BRIEF DESCRIPTION OF THE DRAWINGS

The invention is further described by way of example with reference to the accompanying drawings, wherein:

FIG. 5A is a perspective view of a delivery mechanism for transporting and deploying the frame construction;

FIG. 5B is perspective view of the delivery mechanism with an inner shuttle cannula thereof rotated through 180°;

DETAILED DESCRIPTION OF THE INVENTION

Figure 1A:
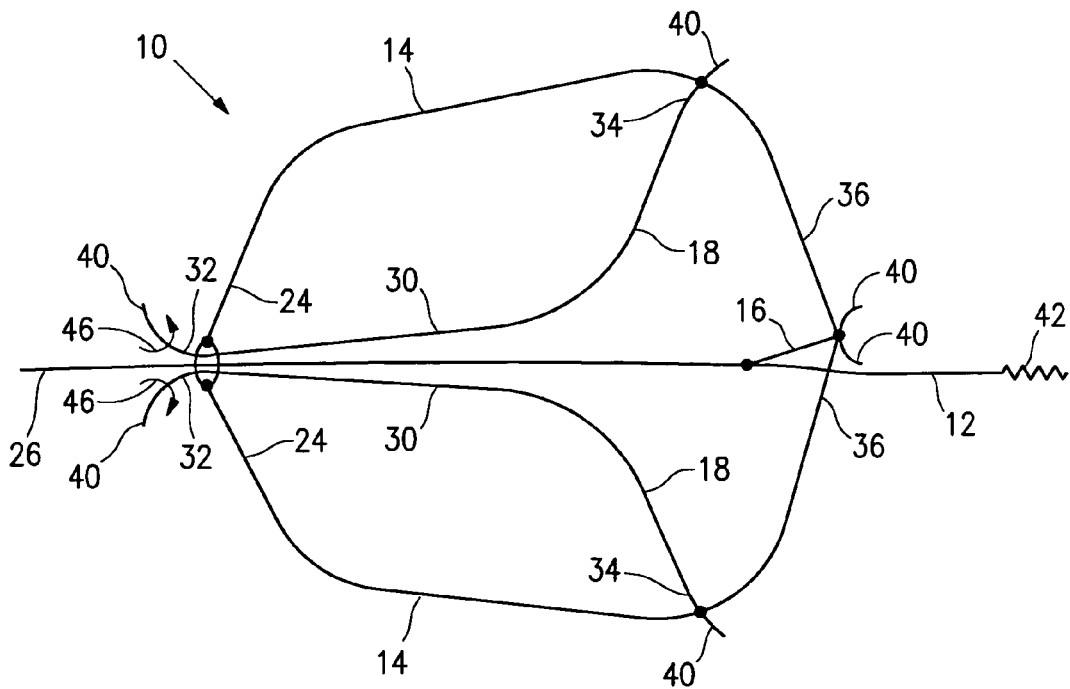
FIGS. 1A and 1B are top plan and side views of a frame construction for a device according to an embodiment of the invention, wherein the frame construction is in an open position.
Figure 1B:
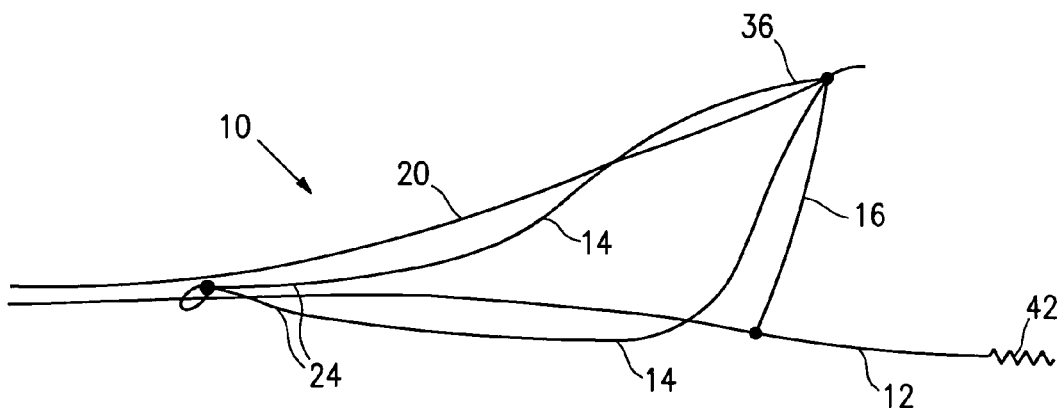

FIGS. 1A and 1B illustrate a frame construction 10 of a device according to an embodiment of the invention. Not shown in FIGS. 1A and 1B is a membrane that is secured to the frame construction 10 and a delivery mechanism used for delivering and deploying the frame construction 10 and the membrane. The frame construction 10 is assembled from seven wires, including an anchor wire 12, two partition rim wires 14, a anchor stem wire 16, two rim wire extenders 18 (FIG. 1A only), and a membrane pull wire 20 (FIG. 1B only).

Proximal ends 24 of the partition rim wires 14 are secured to one another, hinged relative to one another, and slidably located on a proximal portion 26 of the anchor wire 12. The rim wire extenders 18 have central portions 30 that extend along the anchor wire 12. Proximal portions 32 of the rim wire extenders 18 are bent outwardly away from the anchor wire 12. Distal ends 34 of the rim wire extenders 18 are secured to the partition rim wires 14. Distal ends 36 of the partition rim wires 14 are secured to one another and to a distal end of the anchor stem wire 16. Ends of the wires 14, 16, and 18 are formed into hooks 40 that can be used for anchoring to tissue of a myocardium. A distal end of the anchor wire 12 is formed into an anchoring screw 42 that can also anchor to a myocardium. Although the hooks 40 and anchoring screw 42 are shown, it should be understood that other anchoring formations may be used, such as clamps, staples, etc.

Figure 2:
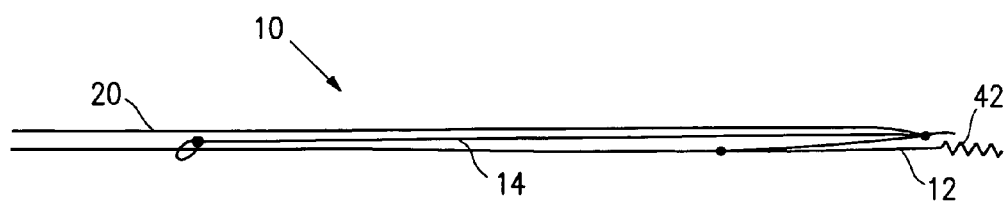
FIG. 2 is a side view of the frame construction in a collapsed condition.

As illustrated in FIG. 2, the entire frame construction 10 is initially collapsed, which allows the frame construction 10 to be located within a catheter and to be transported within the catheter into a ventricle of a heart. The anchoring screw 42 can then be turned into a myocardium of the heart, thereby anchoring the distal end of the anchor wire 12 to the myocardium.

Figure 3:
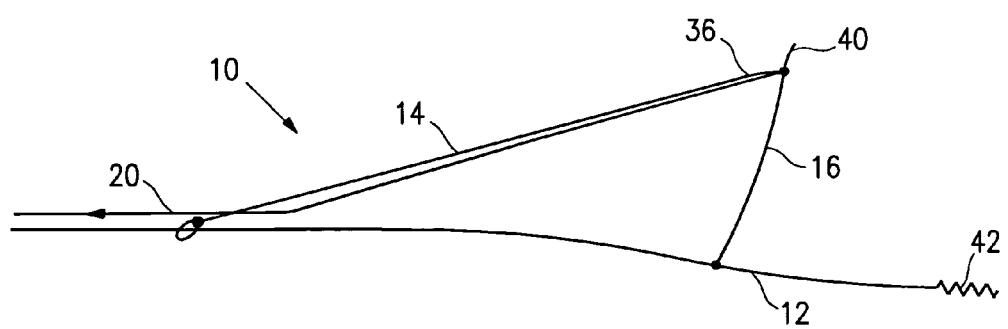
FIG. 3 is a view similar to FIG. 2, with partition rim wires of the frame construction being deployed by pulling on a membrane pull wire.

Next, as illustrated in FIG. 3, a proximal end of the membrane pull wire 20 is retracted, which pivots the anchor stem wire 16 about its proximal end at the anchor wire 12. Distal ends 36 of the partition rim wires 14, connected to the distal end of the anchor stem wire 16, then move away from the anchor wire 12. The anchoring hook 40 formed by the distal end of the anchor stem wire 16, also separates from the anchoring screw 42 and can be moved into contact with the myocardium at a location distant from the anchoring screw 42.

Figure 4A:
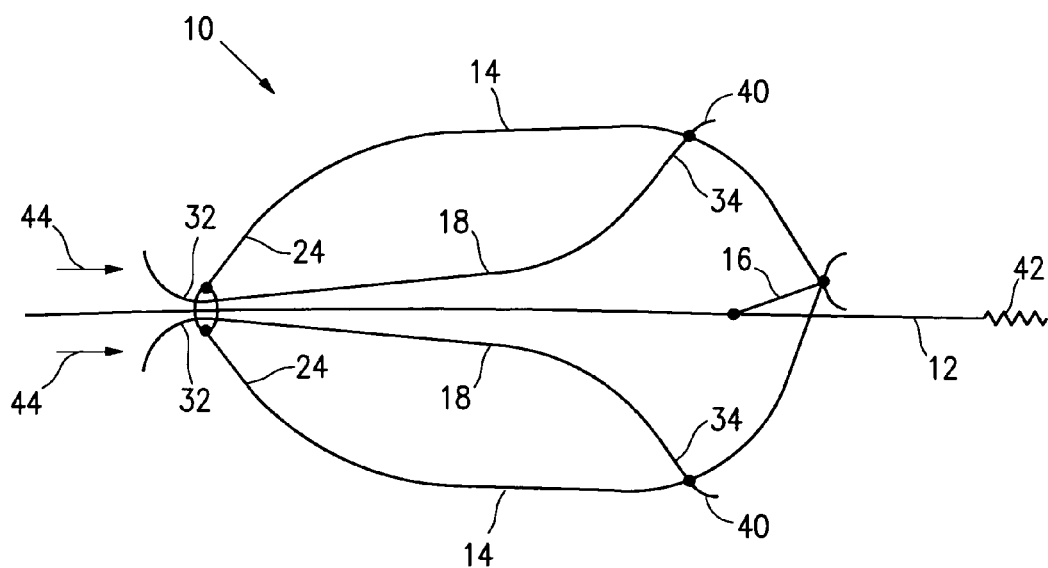
FIGS. 4A and 4B are plan and side views of the frame construction, wherein the partition rim wires are expanded by depressing rim wire extenders.
Figure 4B:
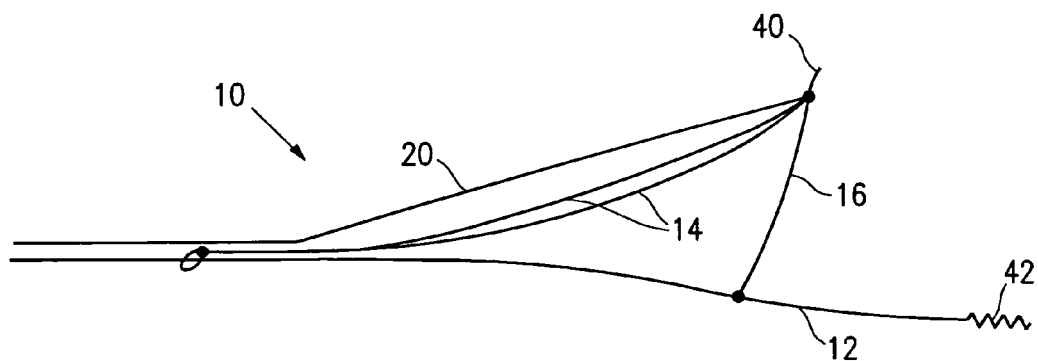

As illustrated in FIGS. 4A and 4B, the proximal ends 32 of the rim wire extenders 18 are then advanced in a direction 44, i.e., toward the anchoring screw 42. The distal ends 34 of the rim wire extenders 18 being connected to the partition rim wires 14, move the partition rim wires 14 outwardly away from one another, with the proximal ends 24 of the partition rim wires 14 sliding along the anchor wire 12 in a direction toward the anchor screw 42.

Referring again to FIG. 1A, the proximal ends 32 of the rim wire extenders 18 can then be rotated in directions 46. Rotation of the rim wire extenders 18 rotates the partition rim wires 14. The partition rim wires 14 are rotated so that they are positioned adjacent to a myocardium in the heart. The anchoring hooks 40 at the end of the rim wire extenders 18 can then also be inserted into the myocardium of the heart. With the anchoring hooks 40 engaged with the myocardium and the partition rim wires 14 located against the myocardium, the anchoring hooks 40 at the proximal ends 32 of the rim wire extenders 18 can then also be inserted into the myocardium.

FIG. 5A illustrates a delivery mechanism 50 that may be used for deploying the frame construction as hereinbefore described. The delivery mechanism 50 includes an outer delivery catheter sheath 52, an outer shuttle cannula 54, an inner shuttle cannula 56, and an inner guide cannula 58, one coaxially located within the other.

The outer and inner shuttle cannulas 54 and 56 have key formations 60 and 62 respectively, and retaining openings 66 are formed in the inner shuttle cannula 56. The proximal ends 32 of the rim wire extenders 18 are inserted through the openings 66, thereby securing the rim wire extender 18 to the inner shuttle cannula 56. The anchor wire 12 and the membrane pull wire 20 both extend through the inner guide cannula 58.

The inner guide cannula 58 initially extends approximately to the anchoring screw 42. Once the anchoring screw 42 is connected to the myocardium, the inner guide cannula 58 is withdrawn into the inner shuttle cannula 56. The membrane pull wire 20 is then retracted to elevate the partition rim wires 14 (as illustrated in FIG. 3). The outer and inner shuttle cannulas 54 and 56 are then advanced in a distal direction within the outer delivery catheter sheath 52. Advancement of the outer and inner shuttle cannulas 54 and 56 open the partition rim wires 14 (as illustrated in FIGS. 4A and 4B). The outer and inner shuttle cannulas 54 and 56 can then be rotated within the outer delivery catheter sheath 52, so that the partition rim wires 14 are rotated (as illustrated in FIGS. 1A and 1B). The inner shuttle cannula 56 is then partially retracted into the outer shuttle cannula 54 until the proximal ends 32 of the rim wire extenders 18 are partially pushed through the openings 66 by a proximal surface of the key opening formation 60.

As illustrated in FIG. 5B, the inner shuttle cannula 56 is then rotated within the outer shuttle cannula 54. Anchoring hooks that are located within the inner shuttle cannulas 56 can then be inserted into the myocardium. The inner shuttle cannula 56 can then be retracted so that the proximal ends 32 of the rim wire extenders 18 disengage therefrom. Mechanisms which are known in the art may be used for disengaging the anchor wire 12 and the membrane pull wire 20, whereafter the delivery mechanism 50 can be removed from the heart.

Figure 6A:
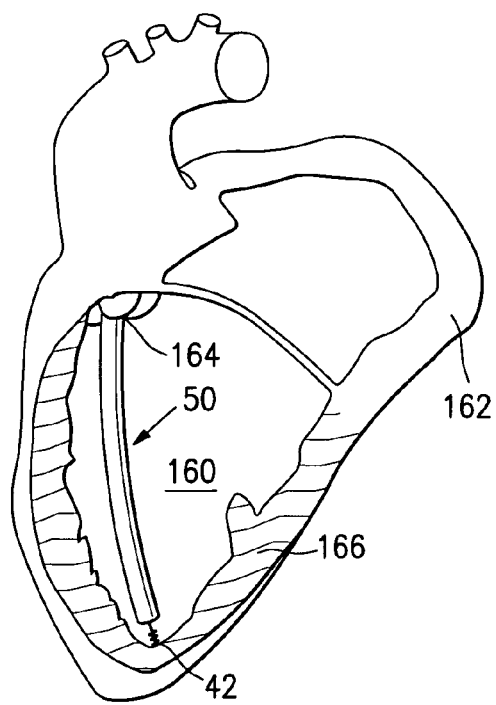
FIGS. 6A through 6D are cross-sectional side views through a heart.
Figure 6B:
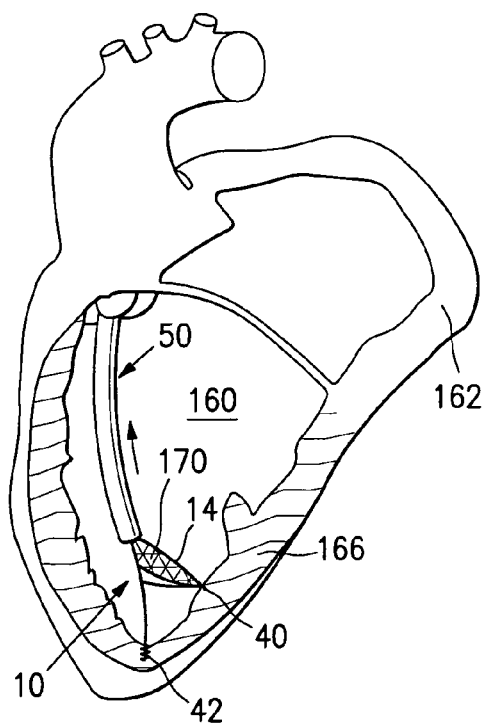
Figure 6C:
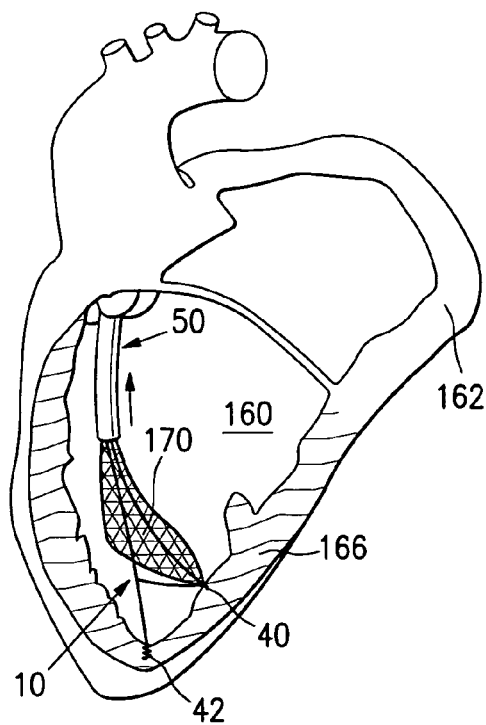
Figure 6D:
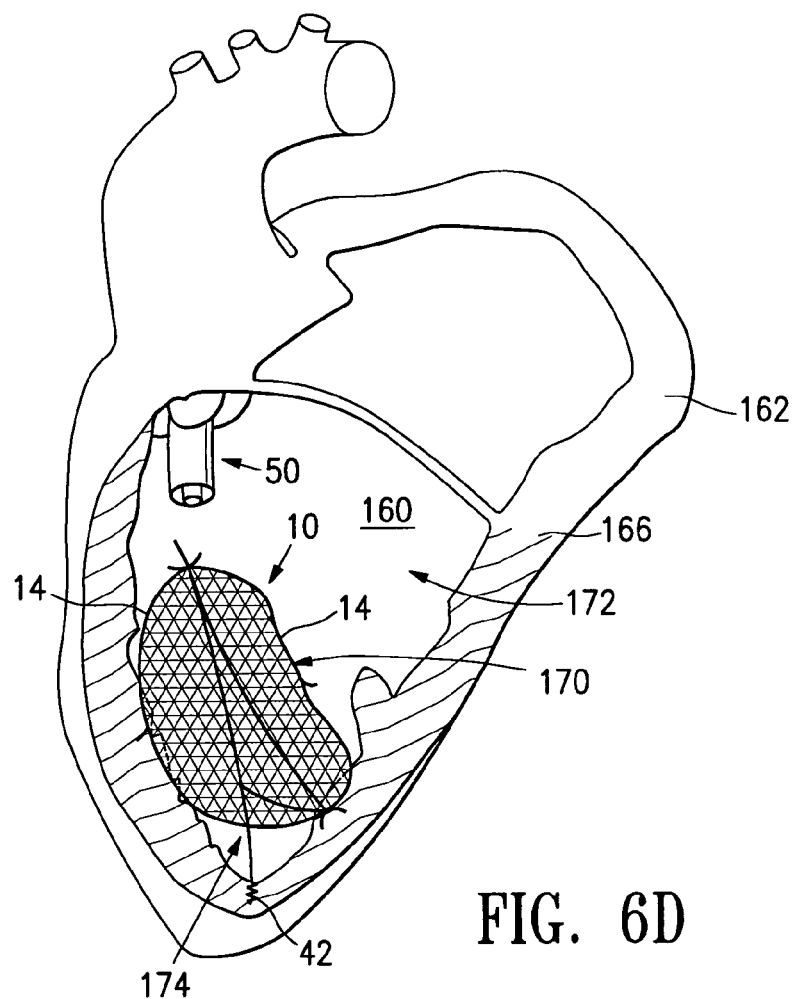

FIGS. 6A to 6E illustrate deployment of the device within the left ventricle 160 of a heart 162. As illustrated in FIG. 6A, the delivery mechanism 50 is inserted through the aortic valve 164 of the heart 162, and the distal anchoring screw 42 is connected to the myocardium 166 of the heart 162. As illustrated in FIG. 6B, the partition rim wires 14 are elevated, and the anchoring hooks 40 at ends thereof are secured to the myocardium 166. As illustrated in FIGS. 6C and 6D, the delivery mechanism 50 is withdrawn, which leaves the frame construction 10 secured to the myocardium.

Figure 6E:
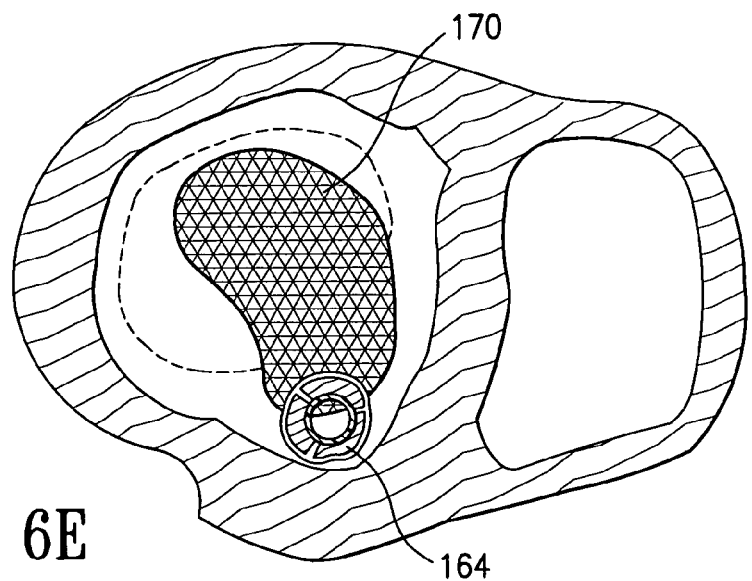
FIG. 6E is a cross-sectional top plan view through the heart, illustrating deployment of the device within a ventricle of the heart.

Also forming part of the device is a membrane 170 which has a periphery secured to the partition rim wires 14. The partition rim wires 14 are located on the myocardium 166, so that the membrane 170 forms a division between first and second volumes 172 and 174 of the ventricle 160. FIG. 6E illustrates the positioning of the membrane 170 with respect to the aortic valve 164.

Figure 7A:
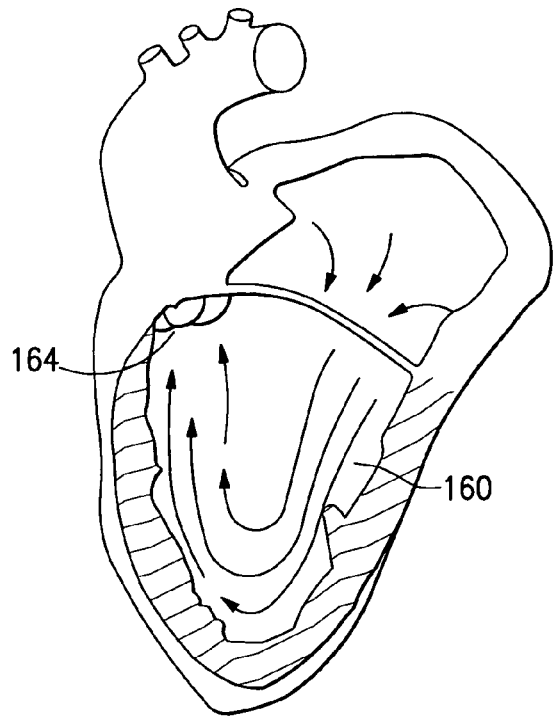
FIGS. 7A to 7C are cross-sectional side views illustrating the flow pattern within the ventricle before and after a membrane of the device is deployed within the ventricle.

FIG. 7A illustrates the flow through the ventricle 160 before an aneurysm is formed out of the ventricle 160. Blood flows through a mitral valve into the ventricle 160, through the ventricle 160, and then exits the ventricle 160 through the aortic valve 164.

Figure 7B:
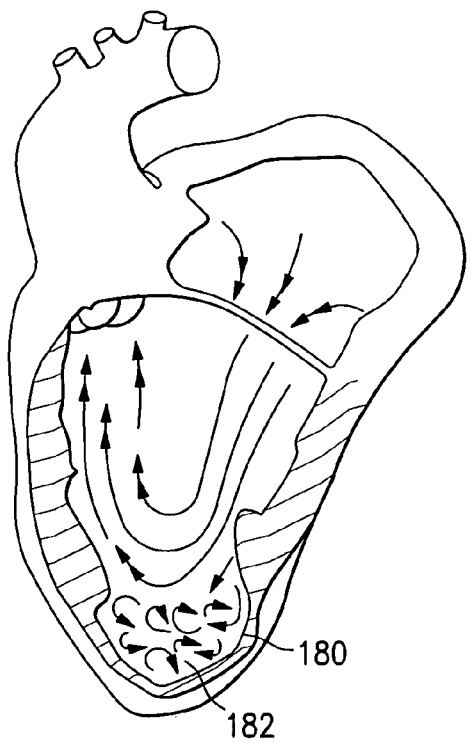

FIG. 7B illustrates the flow within the ventricle 160 after an aneurysmic bulge 180 is formed out of the ventricle 160. Small eddy currents 182 are formed within the aneurysmic bulge 180, while flow within an upper portion of the ventricle 160 remains substantially laminar.

Figure 7C:
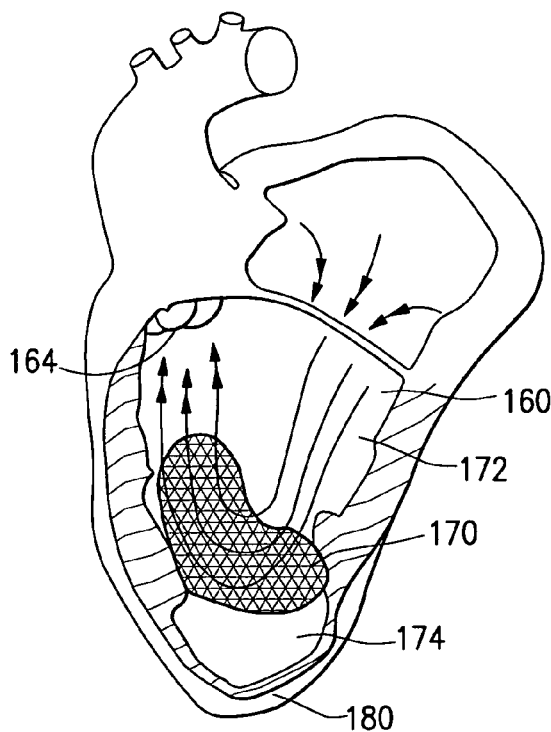

As illustrated in FIG. 7C, the membrane 170 forms a division between a hemodynamic volume 172 of the ventricle 160 and a relatively hemostatic volume 174 partially formed by the aneurysmic bulge 180. The blood now flows through the mitral valve into the hemodynamic volume 172, through the hemodynamic volume 172, and then out of the aortic valve 164. The membrane 170 segregates the relatively hemostatic volume 174 from the normal flow area of the heart within the hemodynamic volume 172.

FIGS. 8A to 8D illustrate the use of the membrane 170 to create a thrombus. Blood can still pass through fenestrations in the membrane 170 into and out of the hemostatic volume 174. The fenestrations reduce pressures that act on the membrane 170, and so reduce stresses within the membrane 170, the frame construction to which the membrane 170 is mounted, and to the myocardium to which the frame construction 10 is secured. The flow characteristics through the hemostatic volume 174 allow for the growth of the thrombus from the base of the hemostatic volume 174. The thrombus grows to encompass all of the hemostatic volume 174, so as to provide support for the membrane 170. Any remaining stresses within the membrane 170 are thereby substantially diminished. The thrombus shrinks over an ensuing period of time, with the membrane 170 having been rendered inconsequential by having been fully incorporated and endothelialized, forming a new inner wall of the ventricle 160.

Figure 8A:
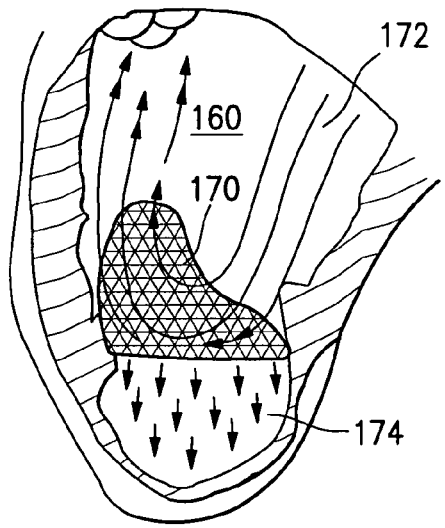
FIGS. 8A to 8D are cross-sectional side views illustrating the use of the membrane to grow a thrombus within the ventricle.

With specific reference to FIG. 8A, blood enters from the hemodynamic volume 172 through the fenestrations into the hemostatic volume 174, pressurizes the hemostatic volume 174, and then may flow through the fenestrations back into the hemodynamic volume 174. The fenestrations, by allowing blood to flow therethrough, reduce pressures that act on the membrane 170 and contribute to the predictable propagation of a thrombus within the hemostatic volume 174.

Figure 8B:
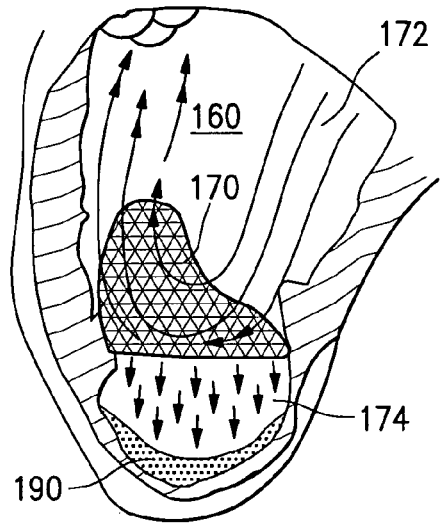

The flow of blood through the hemostatic volume 174 is slow when compared to circular flow patterns 182 of FIG. 7B. The flow within the hemostatic volume 174 near the membrane 170 is primarily turbulent, due to the disruption of flow created by the membrane 170 and the relatively small sizes of the fenestrations. The ongoing flow through the fenestrations in the membrane 170 forestalls the growth of a thrombus on the membrane 170, contributing to the predictable propagation of the thrombus. Additionally, the membrane 170 is preferably thrombolytic to forestall growth of a thrombus on the membrane 170. The flow pattern within a base of the hemostatic volume 174 is primarily turbulent. With reference to FIG. 8B, such turbulent flow permits the creation and growth of a thrombus 190 on a base of the hemostatic volume 174. The location of the thrombus 190 does not interfere with flow of blood through the membrane 170 and through the hemostatic volume 174. The fenestrations are large enough so as to allow uncoagulated blood to flow therethrough, but small enough to confine coagulated products of the blood.

Figure 8C:
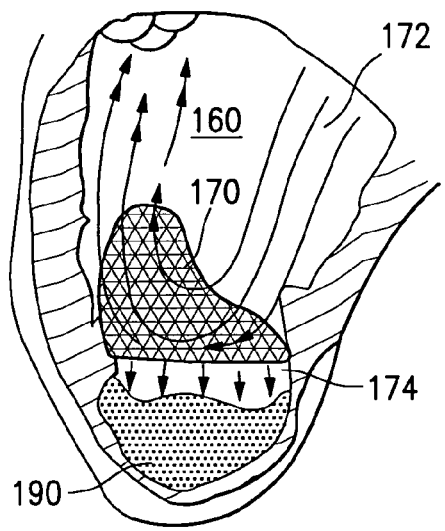
Figure 8D:
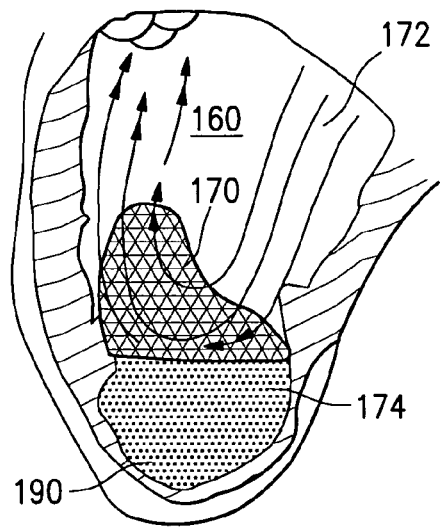

As illustrated in FIGS. 8C and 8D, the thrombus 190 subsequently grows to fill the entire hemostatic volume 174. The thrombus may then grow by an additional degree to lift the membrane 170 slightly. The thrombus is then slightly larger than the size of the original hemostatic volume 174. The growth of the thrombus up to the stage of FIG. 8D is typically between six and 12 hours, but may be between one hour and thirty days. The thrombus now provides support for the membrane 170, so that pressures created within the hemodynamic volume 172 are transferred through the membrane 170 onto the thrombus 190. Strain within the membrane 170 and forces acting on the myocardium of the heart, which are already low due to the inclusion of the fenestrations, are thereby further reduced to substantially zero.

A lining on an inner surface of the myocardium of the heart grows to form an endothelial lining over the membrane 170. The endothelial lining forms a wall that ties opposing sides of the myocardium together, and so further assists in absorbing pressures created within the hemodynamic volume 172. Thrombolytic agents may be applied to the membrane 170 to prevent clot formation, but these thrombolytic agents should not persist for any longer than is necessary to form the thrombus 190, if such thrombolytic agents would prevent endothelialization.

Over time, the thrombus 190 may begin to shrink, and a portion of the myocardium surrounding the thrombus 190 may begin to recede toward the membrane 170. The hemostatic volume 174 may decrease by at least 20% in twelve months. In order to allow for the thrombus to shrink, the frame construction 10 may at least have portions thereof that are bio-absorbable, or can bend to allow for the myocardium to recede toward the membrane 170.

It can thus be seen that pressures on the membrane 170 are reduced by providing fenestrations in the membrane 170. The fenestrations also create a flow pattern within the hemostatic volume 174, which promotes growth of the thrombus 190. The growth of the thrombus 190 is promoted from a base of the hemostatic volume 174 toward the membrane 170, so that the thrombus 190 eventually lifts the membrane 170 and then forms the primary structure which further absorbs pressures from the hemodynamic volume 172.

It is believed that at least some of the fenestrations in the membrane 170 should be at least 30 microns wide to allow for a sufficient blood flow rate therethrough. It is also believed that none of the fenestrations should be larger than 2000 microns, preferably no larger than 500 microns, so as to create the correct flow pattern within the hemostatic volume 174 and promote the creation and growth of the thrombus 190. The fenestrations preferably form between 25% and 75% of the entire area of the membrane 170, and there are typically at least 1000 of the fenestrations.

The membrane 170 is preferably made of a material which is non-thrombogenic. Materials that are non-thrombogenic may include Nomex™, Kevlar™, Spectra™, PET, PTFE, PGA, PLA, PEEK, Nylon, NITINOL, stainless steel, Eligiloy™, gold-plated molybdenum, or platinum. In order to be bioabsorbable, the membrane 170 may be made of a material such as PGA, PLA, pericardium, or small intestinal submucosa. These materials are all intervascularly biocompatible. Other membrane materials include Gore-Tex®, polyethylene terephthalate, polypropylene mesh, and the membrane may be formed of a mesh.

Figure 9A:
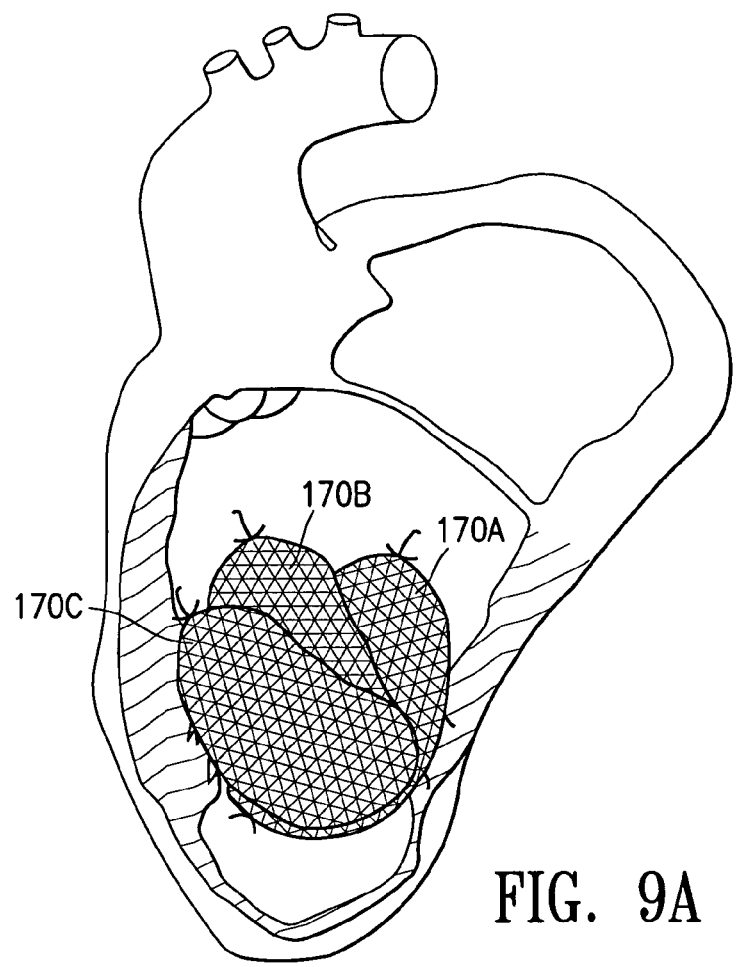
FIGS. 9A and 9B are cross-sectional side and cross-sectional top plan views respectively, illustrating the use of multiple membranes.
Figure 9B:
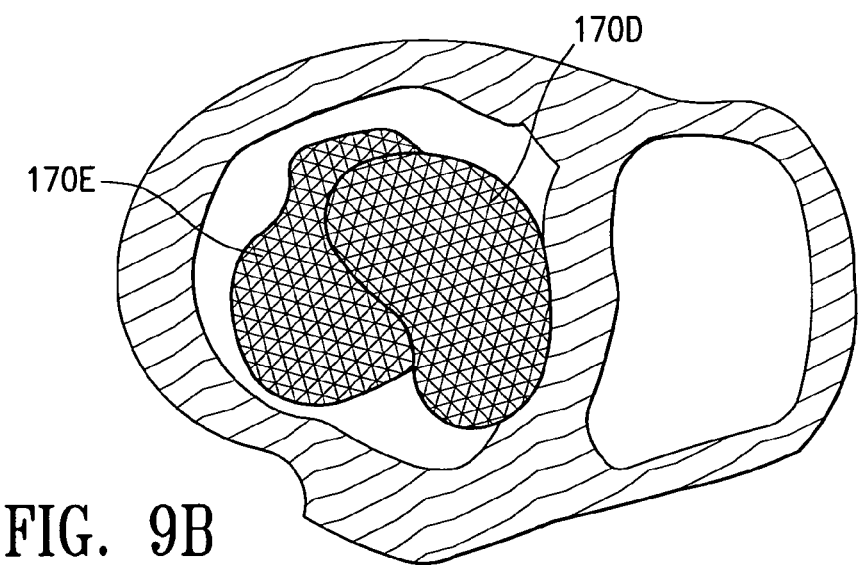

FIG. 9A illustrates the use of multiple devices, each having a respective membrane 170A-C. The orientations of the devices are such that different locations of hypokinetic segments of the heart can be isolated. FIG. 9B illustrates the positioning of two membranes 170D and 170E in an overlapping manner as viewed from a mitral valve annulus. While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed is:

1. A method of treating a patient's heart to improve cardiac function, comprising:
   (a) inserting a membrane in a collapsed configuration having a plurality of fenestrations and at least one anchor formation connected to the membrane into a left ventricle of the patient's heart;
   (b) expanding the membrane within the left ventricle of the patient's heart; and
   (c) securing the membrane with at least one anchor element on the at least one anchor formation within the distal apical region of the left ventricle by inserting the at least one anchor element into a wall of the left ventricle to partition the left ventricle into a main productive portion and a secondary, distal apical non-productive portion, the membrane and the left ventricle wall forming the boundaries of the non-productive portion within the left ventricle, with blood entering the productive portion through a first respective heart valve and leaving the productive portion through a second respective heart valve and with the fenestrations of the membrane being sufficiently large to allow blood flow from the productive portion therethrough into the non-productive portion, but sufficiently small so that thrombus grows within the non-productive portion, wherein the membrane is at least partially absorbed to form a new inner wall of the ventricle.

2. The method of claim 1, wherein the thrombus grows within the non-productive portion because the membrane causes slower flow of blood within the non-productive portion than within the productive portion.

3. The method of claim 2 wherein, after a further period of time, the non-productive portion decreases in size.

4. The method of claim 3, wherein the non-productive portion decreases at least 20% in 12 months.

5. The method of claim 1 wherein, after an initial period of time, the thrombus substantially fills the non-productive portion, occluding the non-productive portion.

6. The method of claim 5, wherein the initial period of time is between one hour and thirty days.

7. The method of claim 5, wherein, after a further period of time, surfaces of the membrane facing the productive portion endothelialize.

8. The method of claim 1, wherein at least surfaces of the membrane facing the productive portion are non-thrombogenic.

9. The method of claim 1 wherein thrombus is formed within the secondary non-productive portion of the partitioned chamber due to hemostasis therein.

10. The method of claim 9 wherein the secondary non-productive portion of the partitioned heart chamber is filled with thrombus.

11. The method of claim 1, wherein each fenestration is between 50 to 2000 microns wide.

12. The method of claim 11, wherein each fenestration is less than 1000 microns wide.

13. The method of claim 11, wherein there are at least 1000 fenestrations.

14. The method of claim 11, wherein the fenestrations form between about 25% to 75% of an area of the membrane.

15. The method of claim 11, wherein the membrane does not have a fenestration that is larger than 2000 microns.

16. A method of treating a patient's heart to improve cardiac function, comprising:
   (a) inserting a membrane in a collapsed configuration having a plurality of fenestrations and at least one anchor formation connected to the membrane into a left ventricle of the patient's heart;
   (b) expanding the membrane within the left ventricle of the patient's heart; and
   (c) anchoring the membrane with at least one anchor element on the at least one anchor formation within the distal apical region of the ventricle by inserting the at least one anchor element into a wall within the left ventricle to partition the left ventricle into a main productive portion and a secondary, distal apical non-productive portion, the membrane and the left ventricle wall forming the boundaries of the non-productive portion within the left ventricle, with blood entering the productive portion through a first respective heart valve and leaving the productive portion through a second respective heart valve and with the fenestrations of the membrane being sufficiently large to allow blood flow from the productive portion therethrough into the non-productive portion, but the fenestrations being sufficiently small to cause slower flow of blood within the non-productive portion than in the productive portion so that thrombus grows within the non-productive portion, and wherein at least 25% of the membrane is absorbed in five years.

17. A method of treating a patient with congestive heart failure, comprising:
   (a) providing a membrane that is formed at least in part of a bioabsorbable material which has a plurality of fenestrations and at least one anchor formation connected to the membrane;
   (b) expanding the membrane within a chamber of the patient's heart; and
   (c) securing the expanded membrane with at least one anchor element on the at least one anchor formation within the distal apical region of the chamber by inserting the at least one anchor element into a wall of the chamber to partition the chamber into a main productive portion and a secondary, distal apical non-productive portion, the membrane and the chamber forming the boundaries of the non-productive portion within the left ventricle, wherein the absorption of the membrane forms a new inner wall of the chamber.

18. The method of claim 17 wherein the heart chamber is the patient's left ventricle.

19. The method of claim 18 wherein the membrane is reinforced with a frame having a plurality of ribs.

20. The method of claim 17 wherein the membrane is reinforced.

21. The method of claim 20 wherein the secondary non-productive portion of the partitioned heart chamber fills with thrombus within thirty days from the partitioning of the heart chamber.

22. The method of claim 17 wherein the fenestrations are large enough to allow blood to flow therethrough from the main productive portion of the heart chamber to the secondary non-productive portion of the heart chamber.

23. The method of claim 17 wherein the fenestrations are small enough to block passage of thrombus from the secondary non-productive portion of the partitioned heart chamber to the primary functional portion of the partitioned chamber.

24. The method of claim 17 wherein a face of the membrane defines in part the primary functional portion of the partitioned heart chamber.

25. The method of claim 24 wherein a face of the membrane defining in part the primary productive portion of the heart chamber is endothelialized.

26. The method of claim 17 wherein fenestrations in the membrane are at least 50 micrometers wide.

27. The method of claim 17 wherein fenestrations in the membrane are not more than 2000 microns wide.

28. The method of claim 17 wherein fenestrations in the membrane are not more than 1000 microns wide.

29. The method of claim 17 wherein the fenestrations in the membrane form about 25 to about 75% of the face of the membrane defining at least in part the primary productive portion of the partitioned heart chamber.

30. The method of claim 29 wherein bioabsorbable materials are selected from the group consisting of polyglycolic acid, polylactic acid, pericardium and small intestine mucosa.

31. The method of claim 17 wherein the membrane defining at least in part the primary productive portion of the heart chamber is non-thrombogenic.

32. The method of claim 17 wherein the membrane is delivered to the patient's heart chamber in a collapsed configuration.

* * * * *